United States Patent
Bohner et al.

(10) Patent No.: US 9,205,174 B2
(45) Date of Patent: Dec. 8, 2015

(54) BONE GRAFT SUBSTITUTE IN THE FORM OF AN IMPLANTABLE THREE-DIMENSIONAL SCAFFOLD AND METHOD OF MANUFACTURING SAME

(71) Applicant: Mathys AG Bettlach, Bettlach (CH)

(72) Inventors: Marc Bohner, Grenchen (CH); Reto Luginbühl, Spiez (CH)

(73) Assignee: MATHYS AG BETTLACH, Bettlach (CH)

( * ) Notice: Subject to any disclaimer, the term of this patent is extended or adjusted under 35 U.S.C. 154(b) by 0 days.

(21) Appl. No.: 14/284,223

(22) Filed: May 21, 2014

(65) Prior Publication Data

US 2014/0257514 A1    Sep. 11, 2014

Related U.S. Application Data

(63) Continuation of application No. 13/582,957, filed as application No. PCT/CH2010/000063 on Mar. 9, 2010.

(51) Int. Cl.

| | |
|---|---|
| A61F 2/28 | (2006.01) |
| A61L 27/42 | (2006.01) |
| A61K 9/00 | (2006.01) |
| A61L 27/54 | (2006.01) |
| A61L 31/16 | (2006.01) |
| A61L 31/02 | (2006.01) |
| A61L 31/14 | (2006.01) |
| A61K 33/14 | (2006.01) |
| A61K 33/42 | (2006.01) |
| A61L 27/56 | (2006.01) |

(52) U.S. Cl.
CPC .............. *A61L 27/425* (2013.01); *A61K 9/0024* (2013.01); *A61K 9/0092* (2013.01); *A61K 33/14* (2013.01); *A61K 33/42* (2013.01); *A61L 27/54* (2013.01); *A61L 27/56* (2013.01); *A61L 31/026* (2013.01); *A61L 31/14* (2013.01); *A61L 31/146* (2013.01); *A61L 31/16* (2013.01); *A61L 2430/02* (2013.01)

(58) Field of Classification Search
CPC .... A61K 9/0024; A61K 9/0092; A61L 27/54; A61L 31/16
See application file for complete search history.

(56) References Cited

U.S. PATENT DOCUMENTS

| | | | |
|---|---|---|---|
| 2003/0049328 A1 | 3/2003 | Dalal et al. | |
| 2004/0096509 A1* | 5/2004 | Hutchens et al. | 424/488 |

FOREIGN PATENT DOCUMENTS

| | | | |
|---|---|---|---|
| WO | 2007/068489 | * | 6/2007 |
| WO | 2007/068489 A2 | | 6/2007 |
| WO | 2009/108935 | * | 9/2009 |
| WO | 2009/108935 A2 | | 9/2009 |

OTHER PUBLICATIONS

International Preliminary Report on Patentability dated Sep. 11, 2012 in corresponding International Patent Application No. PCT/CH2010/000063, filed Mar. 9, 2010.

* cited by examiner

*Primary Examiner* — Carlos Azpuru
(74) *Attorney, Agent, or Firm* — Rankin, Hill & Clark LLP

(57) ABSTRACT

A bone graft substitute in the form of an implantable three-dimensional scaffold that includes calcium phosphate and has pores. The scaffold is impregnated with a calcium and/or phosphate containing substance, and the dissolution rate $DR_S$ of the scaffold is slower than the dissolution rate $DR_D$ of the calcium and/or phosphate containing substance.

30 Claims, 6 Drawing Sheets

BONE GRAFT SUBSTITUTE IN THE FORM OF AN IMPLANTABLE THREE-DIMENSIONAL SCAFFOLD AND METHOD OF MANUFACTURING SAME

CROSS-REFERENCE TO RELATED APPLICATIONS

This application is a continuation of U.S. application Ser. No. 13/582,957, filed Sep. 5, 2012, which application is a U.S. National Stage of PCT/CH2010/000063, filed Mar. 9, 2010.

BACKGROUND OF INVENTION

The invention relates to a bone graft substitute and a method for manufacturing a bone graft substitute.

The following definitions shall be used throughout the description:

Resorption=degradation=process by which a material is removed from the human body.

Scaffold=matrix=porous material.

Macropores=here, we define macropores as pores that have a diameter superior to 30-50 microns.

Micropores=pores with a diameter in the range of 0.1 to 20-30 microns.

Nanopores=pores with a diameter smaller than 100 nm.

Tortuous=tortuous pores are pores that do not have a straight shape (e.g. cylindrical, sphere), but a complex shape, such as a helix, with a large aspect ratio (ratio between the longest and the shortest pore dimension).

Tortuosity=Tortuosity is defined as the ratio between the distance required to join two points in a porous structure through the porous network and the direct distance (with a straight line). Tortuosity values are by definition larger than 1 and often larger than 3.

Calcium phosphate bone graft substitutes have proved to be very good bone graft substitutes: the materials have an excellent biocompatibility and depending on their exact composition, might also be degraded over time and replaced by new bone. One particularly successful material is β-tricalcium phosphate [β-$Ca_3(PO_4)_2$] or shortly [β-TCP].

In past years, many studies have showed the importance of calcium and phosphate ions on the cellular response of bone cells, such as osteoblasts ("bone-forming cells") and osteoclasts ("bone-resorbing cells"). For example, it is known that a small increase of calcium concentration down-regulates osteoclast activity and up-regulates osteoblast activity. Also, it has been shown that increased calcium ion concentrations could trigger osteoblasts to produce bone morphogenetic proteins such as BMP-2 and BMP-4. We have therefore surprisingly found that calcium phosphate bone graft substitutes can be used as drug delivery systems (Ca and phosphate ions being the drugs). The control of calcium and/or phosphate ions release enables also a control of the in vivo properties of calcium phosphate materials.

Generally, it is desirable to have a cell-mediated degradation (e.g. osteoclasts) rather than having a purely physico-chemical degradation, i.e. dissolution, because a cell-mediated degradation ensures that material degradation is not too fast compared to bone formation. However, by just relying on cells to reach material degradation and hence calcium and phosphate release, it is not possible to control the up-regulation or down-regulation of cells in the close surroundings of the material.

It is an object of the invention to provide a bone graft substitute in the form of an implantable three-dimensional scaffold comprising calcium phosphate and having pores and which is impregnated with a calcium and/or phosphate containing substance whereby the dissolution rate $DR_S$ of said scaffold is slower than the dissolution rate $DR_D$ of said calcium and/or phosphate containing substance.

The advantage of the bone graft substitute according to the invention lies in the improved in vivo response of calcium phosphate bone substitutes through selective calcium or phosphate release.

It is a further object of the invention to provide a method for manufacturing a bone graft substitute characterized by impregnating a three-dimensional scaffold comprising calcium phosphate having interconnected pores with a calcium and/or phosphate containing substance; whereby the chemical composition and integrity of said scaffold remains essentially unaffected by said impregnation with said calcium and/or phosphate containing substance. The impregnation can be effected e.g. by spraying, soaking, tipping.

It is a further object of the invention therefore to load a matrix or scaffold that is degraded by cells like β-TCP with a compound that can spontaneously dissolve in vivo, like calcium chloride ($CaCl_2$). The main condition for that purpose is to use a compound that is soluble in vivo. Further in the text, the term of "scaffold" will be used to designate a material resorbed by cell-mediation and the term of "drug" when reference is made to the compound that is soluble in vivo and contains calcium and/or phosphate ions.

Typical calcium phosphate bone graft materials of interest for the scaffold (beside β-TCP) are hydroxyapatite ($Ca_5(PO_4)_3OH$; HA; sintered or non-sintered), dicalcium phosphate ($CaHPO_4$; DCP), octacalcium phosphate ($Ca_8H_2(PO_4)_6.5H_2O$; OCP), α-tricalcium phosphate (α-$Ca_3(PO_4)_2$; α-TCP), α-calcium pyrophosphate (α-$Ca_2P_2O_7$; α-CPP), and β-calcium pyrophosphate (β-$Ca_2P_2O_7$; β-CPP). Of interest are also all calcium phosphates having the general apatite structure according to x-ray diffraction, but not having the exact stoichiometry of hydroxyapatite. This includes for example calcium-deficient hydroxyapatite ($Ca_9(PO_4)_5(HPO_4)(OH)$; CDHA—sometime called "tricalcium phosphate"), carbonated apatites, and more generally all ion-substituted apatites.

All potential scaffolds can also contain some foreign ions in their structure (not only hydroxyapatite). Surprisingly it has been found that many ionic substitutions exist in calcium phosphates. Of particular interest are Mg, Sr, Zn, Si, Na, K, Li and Cl as potential ions for b-TCP, b-CPP, a-CPP and a-TCP. For HA, OCP, DCP and DCPD, the latter ions as well as $CO_3^{-2}$ ions or $SO_4^{-2}$ ions can be used.

Typical calcium-containing ionic materials that can be used as calcium "drug" are calcium chloride (anhydrous: $CaCl_2$, monohydrate: $CaCl_2.H_2O$, dihydrate: $CaCl_2.2H_2O$, or hexahydrate: $CaCl_2.6H_2O$), dicalcium phosphate dihydrate ($CaHPO_4.2H_2O$; DCPD), calcium sulphate dihydrate ($CaSO_4.2H_2O$; CSD), calcium sulphate hemihydrate ($CaSO_4.\frac{1}{2}H_2O$; CSH), calcium sulphate ($CaSO_4$), calcium acetate (anhydrous: $Ca(C_2H_3O_2)_2$, monohydrate: $Ca(C_2H_3O_2)_2.H_2O$, or dihydrate $Ca(C_2H_3O_2)_2.2H_2O$), calcium citrate ($Ca_3(C_6H_5O_7).4H_2O$), calcium fumarate ($CaC_4H_2O_4.3H_2O$), calcium glycerophosphate ($CaC_3H_5(OH_2)PO_4$), calcium lactate ($Ca(C_3H_5O_3)_2.5H_2O$), calcium malate (dl-malate: $CaC_4H_4O_5.3H_2O$, l-malate: $CaC_4H_4O_5.2H_2O$, or malate dihydrogen: $Ca(HC_4H_4O_5)_2.6H_2O$), calcium maleate ($CaC_4H_2O_4.H_2O$), calcium malonate ($CaC_3H_2O_4.4H_2O$), calcium oxalate ($CaC_2O_4$), calcium oxalate hydrate ($CaC_2O_4.H_2O$), calcium salicylate. ($Ca(C_7H_5O_3)_2.2H_2O$), calcium succinate ($CaC_4H_6O_4.3H_2O$), calcium tartrate (d-tartrate:

$CaC_4H_4O_6.4H_2O$; dl-tartrate: $CaC_4H_4O_6.4H_2O$; mesotartrate: $CaC_4H_4O_6.3H_2O$), and calcium valerate ($Ca(C_5H_9O_2)_2$).

Typical phosphate-containing ionic materials that can be used as phosphate "drug" are DCPD, sodium phosphate ($Na_2HPO_4$, $NaH_2PO_4$ or a mixture thereof; non-hydrated or hydrated species like $Na_2HPO_4.2H_2O$, $Na_2HPO_4.7H_2O$, $Na_2HPO_4.12H_2O$, $NaH_2PO_4.H_2O$, $NaH_2PO_4.2H_2O$), calcium glycerophosphate ($CaC_3H_5(OH_2)PO_4$), potassium orthophosphate ($K_3PO_4$), dihydrogen potassium orthophosphate ($KH_2PO_4$), monohydrogen potassium orthophosphate ($K_2HPO_4$), and sodium orthophosphate ($Na_3PO_4.10H_2O$ and $Na_3PO_4.12H_2O$).

Drug Solubility

The solubility of the drug in an aqueous solution having a physiological ionic strength (0.15M) and a pH of 7.4 at 37° C. should be in an adequate range, typically superior to 2 mM, preferably superior to 10 mM. An adequate range appears to be between 10 mM and 1M.

It is particularly useful to have a rather low solubility in physiological conditions because the release rate is accordingly low. However, a low solubility is not adequate for loading because the loaded amount is limited. So, compounds that present a rather low solubility at physiological conditions and a high solubility in other conditions (e.g. $Na_2HPO_4.12H_2O$ is much more soluble at 90° C. than at 37° C.) are interesting because loading can be made in these advantageous conditions and release in physiological conditions is still slow.

Porosity and Pore Size

To load the scaffold with calcium and/or phosphate ions, it is necessary to have a porous scaffold, preferably a scaffold with interconnected pores to allow drug invasion into the pores. A porosity in the range of 40 to 95%, preferably of 55 to 80% is advantageous. It is important to have a slow release, hence implying that the pores should be relatively small (the smaller they are, the slower the release of calcium and phosphate ions will be). Therefore the scaffold should preferably contain micropores or even nanopores. Ideally, at least 10% of the total volume (preferably 20%) should be constituted of micropores or nanopores. It is further advantageous to have tortuous pores. Tortuosity values larger than 5 are preferred.

The ideal pore size depends on the purpose of the bone graft substitute. Small pores (or a large specific surface area) will favor a rapid resorption. So, the resorption rate will increase in the order macropore<micropore<nanopore. However, since the scaffold is meant to be resorbed by cells, a fast resorption also requires the presence of cells.

In other words, scaffolds that have a size superior to a few millimeters should preferably have an interconnected porous network with interconnections larger than 30 to 50 microns to allow bone vessel ingrowth hence leading to rapid bone ingrowth and scaffold resorption. In this case, it is important to have about 30 to 70% of the scaffold volume constituted of macropores, preferably 40 to 60%.

Loading Method

Two main loading methods can be used for manufacturing the bone graft substitute according to the invention (i) Soaking in a Concentrated Drug Solution—

The first possibility is to create a solution containing calcium and/or phosphate ions, soak the porous scaffold into this solution, and let it dry. The pores are then filled with the salt used for the preparation of the calcium and/or phosphate containing solution.

In that respect, it is advantageous to soak the scaffold in a small amount of solution (for example by placing the scaffold vertically into a solution—the solution reaching only the bottom third of the scaffold) and let this dry. During drying, there is constantly a capillary rise from the solution to the top of the scaffold, leading finally to a very large loading of the scaffold with the soluble calcium and/or phosphate entities.

The temperature of the soaking solution is important. Some compounds are much more soluble at low or at high temperature in water, So, it can be advantageous to prepare a solution at e.g. 80° C. and perform the impregnation and drying at the latter temperature.

For other compounds, it can be advantageous to soak the sample with a cold solution (e.g. of 5° C.) and then perform drying at e.g. 60° C. So the solution, soaking and drying temperatures can be varied and the temperature at which the impregnation solution is prepared is of some importance due to the temperature dependence of some solubilities.

It is further advantageous to dry the soaked sample in such a way that the solution can only evaporate through the sample (or scaffold). The beaker or flask containing the soaking solution should be preferably fully covered with a water proof membrane (or material) except where the scaffold is. This approach improves the soaking efficiency.

(ii) Soaking the Scaffold with a Slurry—

The second possibility is to create a slurry containing drug particles and soak the scaffold with the slurry. A requirement is to have drug particles small enough to penetrate the scaffold porosity. Impregnation may be performed under vacuum or under varying pressure cycles, e.g. vacuum—room pressure cycles.

Drying

The procedures of impregnation and drying can require different conditions. Impregnation is preferably performed at slower rate than drying (drying may start when there is no more liquid surrounding the scaffold, but still some liquid within the scaffold).

Impregnation Geometry

Dimension and shape of the impregnation will vary depending on the loading method and the pore size. Nanopores are likely to be completely filled with the soluble calcium and/or phosphate compound. On the other side, macropores are likely to be only partially filled. So, the geometry will vary depending on the pore size.

Release Rate

The dissolution rate $DR_S$ of the scaffold should preferably be null in serum or "simulated body fluid" whereas the dissolution rate $DR_D$ of the drug should be superior to zero in such conditions.

By "simulated body fluid" an aqueous solution is understood which has (at pH 7.4, 37° C., and in equilibrium with a gas atmosphere containing 5% $CO_2$) the ionic strength as serum and the same supersaturation towards hydroxyapatite precipitation than serum.

Not all calcium phosphates can be used as scaffolds because not all of them are insoluble in serum (or simulated body fluid) in physiological conditions (pH 7.4, 37° C., 5% $CO_2$ gas atmosphere). Only calcium phosphates insoluble in serum can be considered as scaffold material. All other calcium phosphates which are soluble in serum (or simulated body fluid) in physiological conditions (pH 7.4, 37° C., 5% $CO_2$ gas atmosphere) can be considered as drug material. When a material is insoluble in serum (or simulated body fluid) in physiological conditions (pH 7.4, 37° C., 5% $CO_2$ gas atmosphere), it means that its dissolution rate $DR_S$ is null. When the material is soluble, then the dissolution rate $DR_S$ is superior to zero (DR>0).

In special embodiments said calcium and/or phosphate containing substance is ionic and/or crystalline. In a further embodiment said calcium and/or phosphate containing substance has a degree of crystallinity higher than 80%, preferably higher than 90%.

In further embodiment said calcium and/or phosphate containing substance is not chemically bound to said scaffold and/or is adhering only physically to said scaffold.

The dissolution rate $DR_D$ as measured in a phosphate-buffered solution (PBS) at pH 7.4 is preferably at least 10 times larger than said dissolution rate $DR_S$. Alternatively the dissolution rate $DR_D$ as measured in an aqueous citric acid solution at pH 3.0 is at least 10 times larger than said dissolution rate $DR_S$. Preferably the dissolution rate $DR_S>0$ and the dissolution rate $DR_D>0$ in serum or simulated body fluid having a pH 7.4 at 37° C. and 5% $CO_2$ in the atmosphere.

Said calcium and/or phosphate containing substance is preferably rigid. The degree of porosity of said scaffold is preferably 40-95%, and most preferably 55 to 80%.

The scaffold may have micropores with a mean diameter $D_{micro}$ smaller than 10 microns, preferably smaller than 1 micron. Further said scaffold may have macropores with a mean diameter $D_{macro}$ in the range of 0.03 to 1 mm. The specific surface area of said scaffold purposefully is superior to 1 $m^2$/g, preferably superior to 4 $m^2$/g. A scaffold with a high SSA value is indicative of a fine micro or nanostructure. Such a fine structure leads to a slow release rate.

The tortuosity of the pores of said scaffold is preferably larger than 3, most preferably larger than 5. Preferably the pores of said scaffold are interconnected and the size of interconnections between the pores is larger than 30 to 50 microns.

In a special embodiment said calcium and/or phosphate containing substance comprises calcium chloride. In a further embodiment said calcium and/or phosphate containing substance comprises $K_2HPO_4$.

The ratio WD/WS between the weight WD of said calcium and/or phosphate containing substance and the weight WS of said scaffold purposefully is comprised in the range of 0.1 to 10, preferably of 0.5 to 2.

In a special embodiment said calcium phosphate of said scaffold is beta-tricalcium phosphate (β-TCP).

Preferably said scaffold has a volume larger than 10 $mm^3$, more preferably larger than 50 $mm^3$.

In a special embodiment the pores of said scaffold are filled with said calcium and/or phosphate containing substance to an extent of 1% to 50 vol.-%, preferably of 5% to 25 vol.-%.

In a special embodiment of the method according to the invention the calcium and/or phosphate containing substance is calcium chloride and the deposition is performed by applying an aqueous solution of calcium chloride to said scaffold. In another embodiment the calcium and/or phosphate containing substance is $K_2HPO_4$ and that the deposition is performed by applying an aqueous solution of calcium chloride to said scaffold. The aqueous solution applied to said scaffold may be dried in an atmosphere having a relative humidity below 10%, preferably below 5%. Preferably said aqueous solution applied to said scaffold is dried for more than 1 day. The aqueous solution purposefully has a concentration of 12.5% to 50%.

In a special embodiment the impregnating is performed in two successive steps. One step may comprise the impregnation with a calcium-containing substance and another step may comprise the impregnation with a phosphate-containing substance. It can be purposeful to use different solvents to this effect and to first load the scaffold with a calcium-containing salt and second load the scaffold with a phosphate-containing salt using a solvent or loading conditions (e.g. T) in/at which the calcium-containing salt is poorly-soluble. It is also possible to load twice the same block, for example by placing the block upside down, since the distribution of the crystalline calcium and/or phosphate containing substances present within the block will not be homogeneously distributed (it is more close to the solution and the block walls, and less in the center and at the top).

A BRIEF DESCRIPTION OF THE DRAWINGS

Several embodiments of the invention will be described in the following by way of examples and with reference to the accompanying drawings in which:

FIG. 1 shows the: relationship between expected and measured $CaCl_2$ loading in the samples. The symbol (▲) represents the calcium chloride loading. The dotted line represents the curve "Expected amount=measured amount". The results obtained with 7 mL of 0.50 g/mL solution are not shown because the samples were very difficult to dry.

FIG. 2 shows the relationship between expected and measured $K_2HPO_4$ loading in the samples. (▲) Measured amount of $K_2HPO_4$ added into the flask+block−measured by determining the difference of weight of the flask+block before and after adding the $K_2HPO_4$ solution (including drying); (Δ) $K_2HPO_4$ loading in the block−measured by determining the difference of weight of the block before and after impregnation. The dotted line represents the expected amount of $K_2HPO_4$ added into the flask and that could potentially "load" the block.

FIG. 3 shows the relationship between expected and measured $Na_2HPO_4.2H_2O$ loading in the samples. (▲) Measured amount of $Na_2HPO_4.2H_2O$ added into the flask+block−measured by determining the difference of weight of the flask+block before and after adding the $Na_2HPO_4.2H_2O$ solution (including drying); (Δ) $Na_2HPO_4.2H_2O$ loading in the block−measured by determining the difference of weight of the block before and after impregnation. The upper dotted line represents the expected amount of $Na_2HPO_4.2H_2O$ added into the flask and that could potentially "load" the block. The lower dotted line represents the expected amount of $Na_2HPO_4$ added into the flask and that could potentially "load" the block, assuming that $Na_2HPO_4.2H_2O$ is transformed into $Na_2HPO_4$ at 95° C.

DETAILED DESCRIPTION OF THE INVENTION

Example 1

Figure 1:
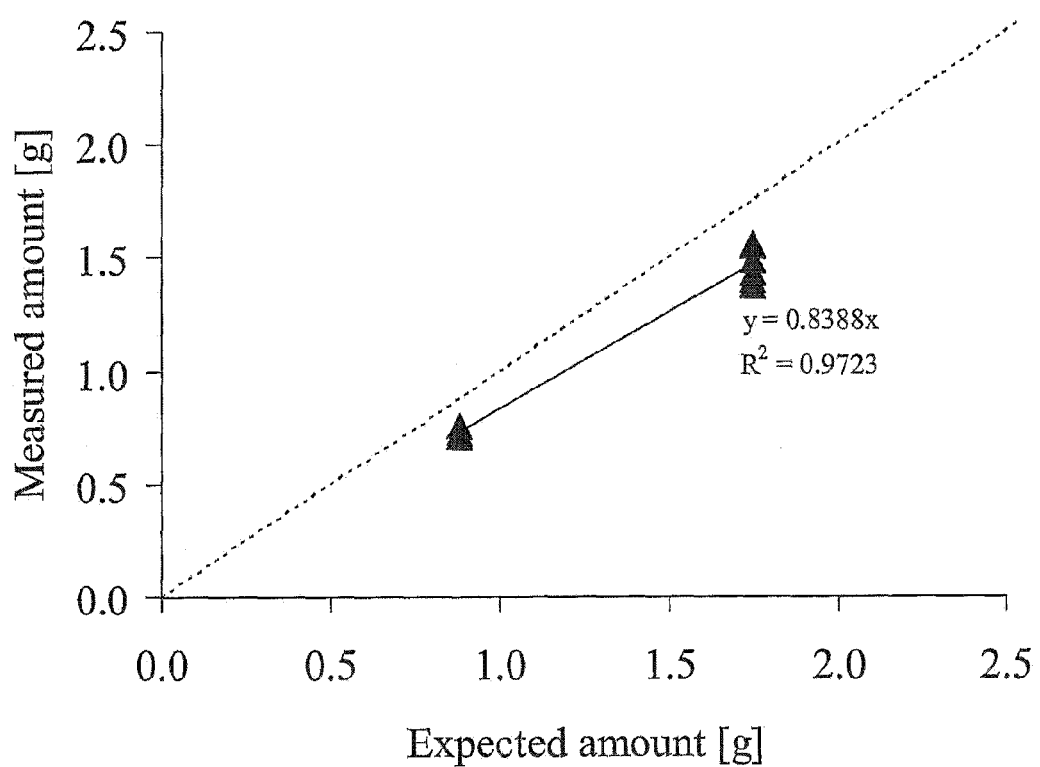

The aim was to perform impregnation tests of porous b-TCP blocks to assess how such blocks can be loaded with a calcium and/or phosphate containing salt The porosity of the porous β-TCP blocks was in the range of 69 to 77%. The porosity consisted of roughly 54% macropores (mean diameter close to 0.3-0.4 mm) and 25-33% micropores (mean diameter in the range of 1-10 micrometers)

The samples were calcined at 500° C. for 1 h prior to the impregnation tests to remove organic residues present on the block surface (without calcination, the samples were so hydrophobic that they were floating in aqueous solutions).

Impregnation tests were performed with a 0.25 g/mL and 0.50 g/mL calcium chloride solution.

A $2^2$ factorial design of experiments with three repeats was performed with the following factors: Factor A: $CaCl_2$ concentration (0.25 or 0.50 g/mL); Factor B: Liquid amount (3.5 or 7.0 mL). Each of the 14×14 mm cylinders was placed standing in a snap cap flask.

The solution was then slowly added to allow impregnation through capillarity. The cylinder top was always protruding out of the solution. The samples were then inserted into the drying cupboard tempered at 60° C. The ventilation of the drying cupboard was set at its maximum.

The weight of the flask+solution+samples was measured at regular interval to determine the point at which constant weight was reached. After 24 h, most samples but 3 (those made with 7 mL 0.50 g/mL solution) appeared to be dry. Therefore, these 9 samples were removed from the flask and the weight was determined without flask. The 3 samples made with 7 mL 0.50 g/mL solution were kept for a longer time. The drying temperature was increased to 80° C. 36 h after the experiment start.

Both Ca solutions were sucked by the porous block within seconds. Since an excess of liquid was used, some solution was left besides the samples.

After drying, a different picture was revealed depending on the soaking solution and the amount: the blocks soaked in calcium chloride appeared mostly "clean", whereas the blocks soaked in 7 mL 0.50 g/mL $CaCl_2$ solution were encrusted in large $CaCl_2$ residues, suggesting that too much $CaCl_2$ was used.

Interestingly, drying was very slow and as soon as the samples were retrieved from the drying cupboard and left in the lab, the block surface became wet, suggesting that the samples were very hygroscopic due to the presence of calcium chloride. After 3.5 days, a liquid could still be found below the crust formed around the samples produced with 7 mL 0.50 g/mL $CaCl_2$.

The amount of calcium chloride present within the samples was slightly lower than expected, perhaps because the calcium chloride crystals used to produce the Ca chloride solution contained water and/or because some of the Ca chloride was left in the snap cap flask. The loading efficiency was close to 84%, without noticeable difference between 7 mL of 0.25 g/mL solution and 3.5 mL of 0.50 g/mL solution.

Example 2

Aim

Perform impregnation tests of porous β-TCP blocks to assess how such blocks can be loaded with a phosphate containing salt Materials and Methods The porosity of the porous β-TCP blocks was in the range of 69 to 77%. The porosity consisted of roughly 54% macropores (mean diameter close to 0.3-0.4 mm) and 25-33% micropores (mean diameter in the range of 1-10 micrometers)

The samples were calcined at 500° C. for 1 h prior to the impregnation tests to remove organic residues present on the block surface (without calcination, the samples were so hydrophobic that they were floating in aqueous solutions).

Impregnation tests were performed with a 0.50 g/mL di-potassium hydrogen phosphate solution ($K_2HPO_4$).

Each of the 14×14 mm cylinders was placed standing in a snap cap flask. The solution was then slowly injected at the bottom of the snap-cap flask to allow impregnation through capillarity. 6 different volumes were injected: 1.8, 2.7, 3.6, 4.5, 5.6 and 6.3 mL.

These volumes correspond to an expected $K_2HPO_4$ amount of 0.9, 1.35, 1.8, 2.25, 2.8 and 3.15 g. Two cylinders were prepared for each solution volume. The cylinder top was always protruding out of the solution. The samples were then inserted into the drying cupboard tempered at 95° C. The ventilation of the drying cupboard was set at its maximum.

The weight of the flask+solution+samples was measured at regular interval to determine the point at which constant weight was reached. The sample weight was determined to assess how much di-potassium hydrogen phosphate was present in the block pores.

Results

The solution was sucked by the porous block within seconds. Since an excess of liquid was used, some solution was left besides the samples, especially with a high liquid amount. The samples looked very good, with hardly any crystals protruding at the sample surface.

The experimental results show a good agreement between measured and expected amount (FIG. 1) of $K_2HPO_4$ present in the β-TCP block. However, it appears that beyond an expected amount of ≈2.5 g, most of the additional $K_2HPO_4$ amount remains in the flask and does not load the β-TCP block.

Example 3

Aim

Perform impregnation tests of porous β-TCP blocks to assess how such blocks can be loaded with a phosphate containing salt Materials and Methods The porosity of the porous β-TCP blocks was in the range of 69 to 77%. The porosity consisted of roughly 54% macropores (mean diameter close to 0.3-0.4 mm) and 25-33% micropores (mean diameter in the range of 1-10 micrometers)

The samples were calcined at 500° C. for 1 h prior to the impregnation tests to remove organic residues present on the block surface (without calcination, the samples were so hydrophobic that they were floating in aqueous solutions).

Impregnation tests were performed with a 0.50 g/mL di-sodium hydrogen phosphate solution ($Na_2HPO_4.2H_2O$).

Since the solubility of di-sodium hydrogen phosphate solution is relatively low at room temperature, the solution was heated up at 95° C. At that temperature, a clear solution was obtained.

Each of the 14×14 mm cylinders was placed standing in a snap cap flask. The solution (kept at 95° C.) was then slowly injected at the bottom of the snap-cap flask to allow impregnation through capillarity. 3 different volumes were injected: 2.7, 4.5, and 6.3 mL, corresponding to 1.35, 2.25 and 3.15 g of $Na_2HPO_4.2H_2O$. Two cylinders were prepared for each solution volume. The cylinder top was always protruding out of the solution.

The samples were then inserted into the drying cupboard tempered at 95° C. The ventilation of the drying cupboard was set at its maximum.

The weight of the flask+solution+samples was measured at regular interval to determine the point at which constant weight was reached. The sample weight was determined to assess how much di-potassium hydrogen phosphate was present in the block pores.

Each sample was then placed into a small porous cage produced by joining together two BD Falcon filters (Mesh size: 70 micrometers). The cage was lowered into a 1 L deionized water. Stirring was performed with a large magnetic bar (6 cm in length) at 50 RPM. The samples were removed from the solution after 1 h or 3 h (1 sample per time and per composition). The samples were then dried at 95° C. and weighed to determine the amount of $Na_2HPO_4.2H_2O$ released during the test.

As control group, 6 β-TCP blocks that had not been impregnated in sodium hydrogen phosphate solution were also tested.

Results

The solution was sucked by the porous block within seconds. Since an excess of liquid was used, some solution was left besides the samples, particularly at a high loading.

Interestingly, the sample surface was not "clean" but covered with a thick material layer.

The amount of material left after drying the flask was lower than expected assuming that all $Na_2HPO_4.2H_2O$ present in the $Na_2HPO_4.2H_2O$ solution is left in the flask. This suggests that either the solution concentration was wrong (for example due to adsorbed water in the initial powder) or the $Na_2HPO_4.2H_2O$ was transformed into $Na_2HPO_4$ during drying. Since there is a very good correlation between the experimental points and the predictions made assuming the presence of $Na_2HPO_4$ (FIG. 1), the latter explanation is probably correct.

The results also show that the loading efficiency decreases with an increase in added $Na_2HPO_4.2H_2O$ amount, suggesting that the block pores cannot be fully filled with $Na_2HPO_4.2H_2O$. The point at which the loading efficiency drastically decreases is close to 1.35 g.

Figure 2:
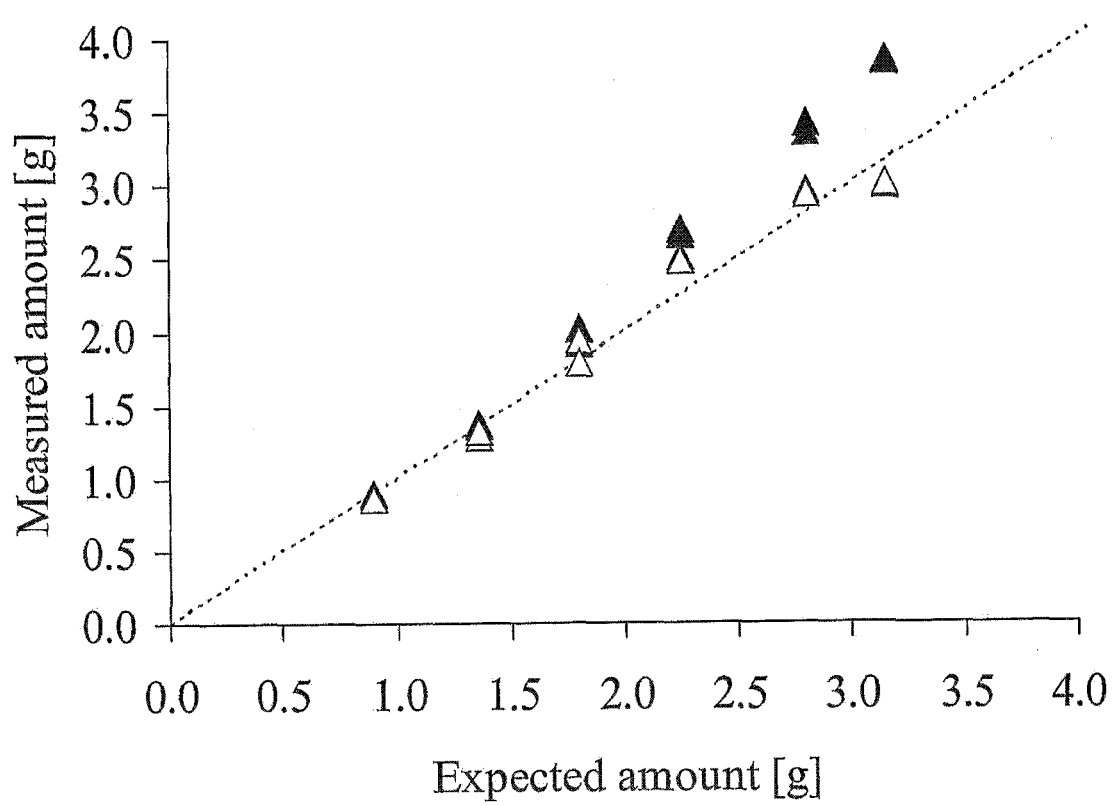
Figure 3:
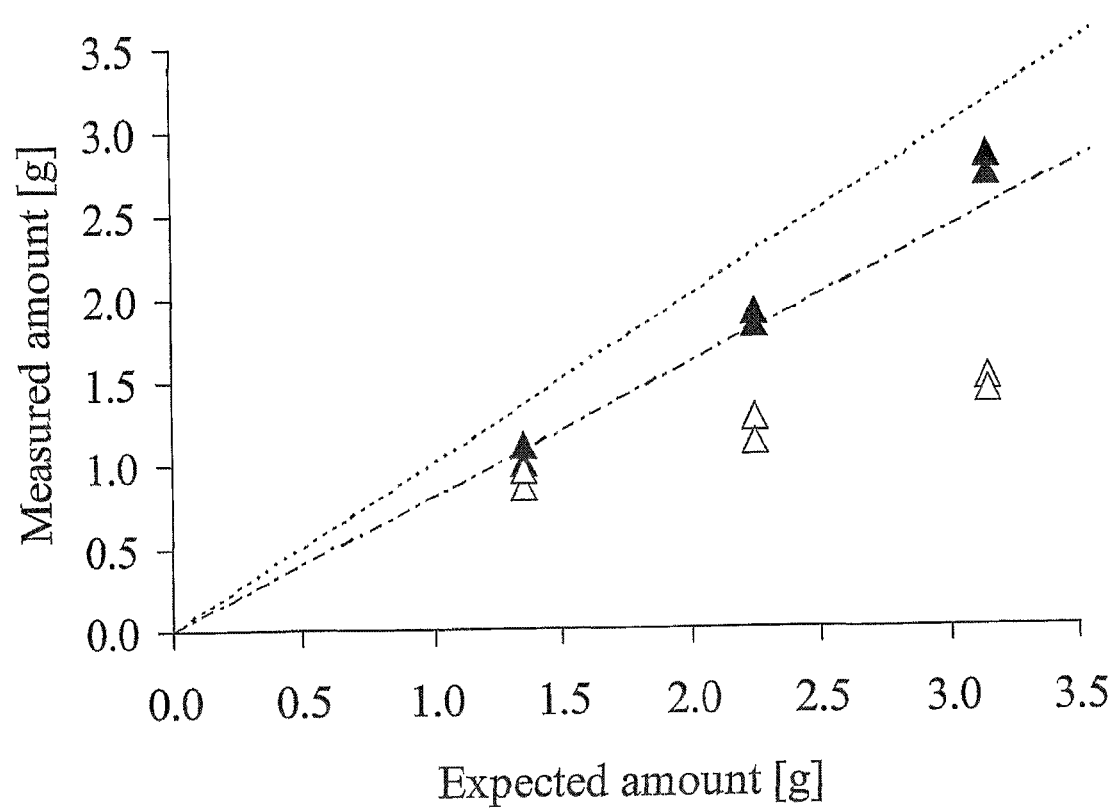
Figure 4:
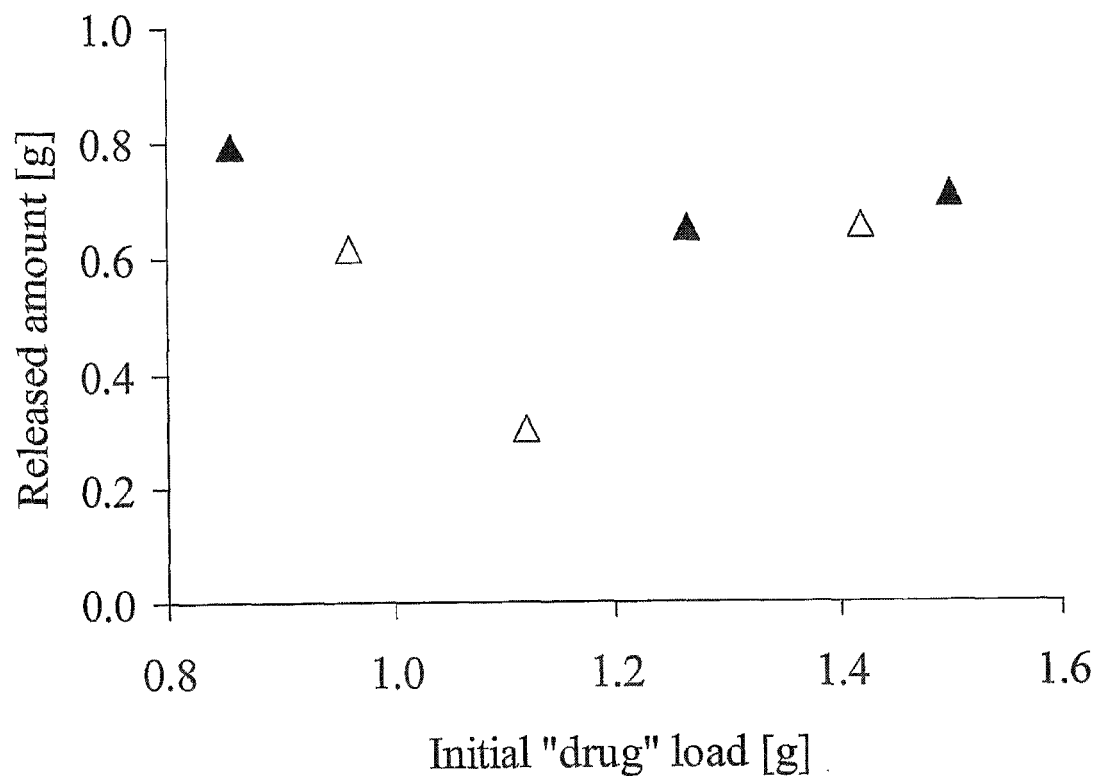
FIG. 4 shows the amount of $Na_2HPO_4.2H_2O$ released during (Δ) 1 or (▲) 3 h incubation in 1 L deionized water according to example 3.
Figure 5:
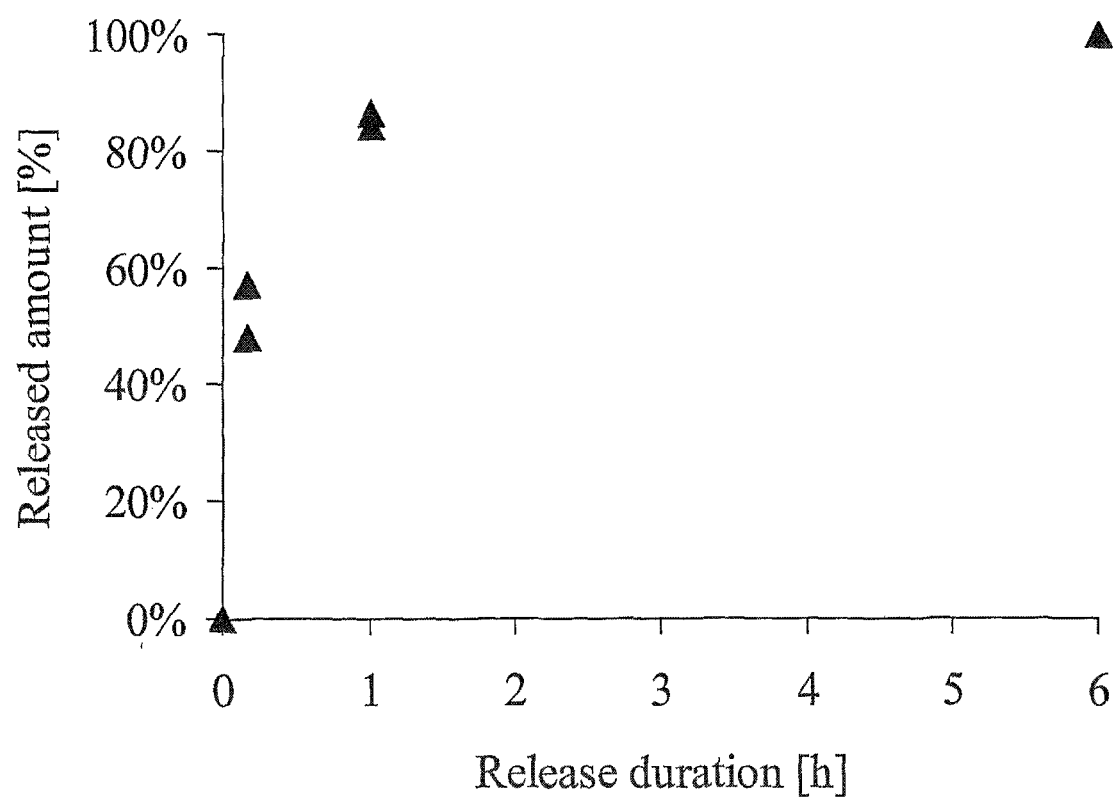
FIG. 5 shows the release of calcium chloride amount (in %) as a function of incubation time in deionized water as described in example 4.
Figure 6:
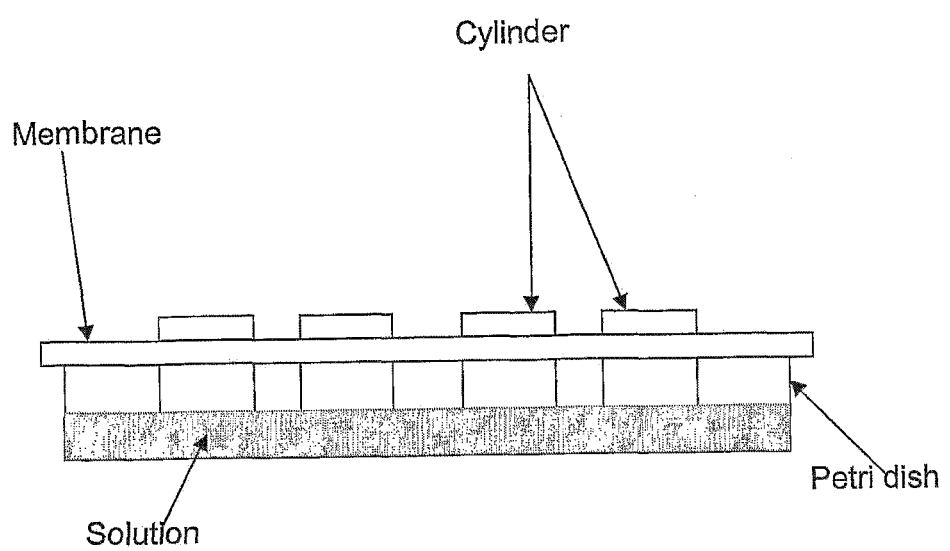
FIG. 6 is a schematic representation of the impregnation test setup (profile) of example 5.

All release solutions contained particles in suspension after the release test suggesting that some particles precipitated in the release solution. This could explain why released $Na_2HPO_4.2H_2O$ amount was not affected by the initial loading and the release duration (FIG. 2). In any case, this experiment shows that the release rate of $Na_2HPO_4.2H_2O$ proceeds relatively slowly, for example compared to the results obtained with $CaCl_2$ in the following example 4.

The mean weight loss of pure β-TCP blocks (without loading) was slightly positive after 3 h (0.005±0.012 g) but not significantly larger than zero, which means that the dissolution rate $DR_D$ of sodium hydrogen phosphate was two order of magnitude larger than the dissolution rate $DR_S$ of β-TCP (since 0.3 to 0.8 grams of sodium hydrogen phosphate were dissolved in the release medium within the same duration).

Example 4

Aim

Assess the rate of calcium chloride release

Materials and Methods

The porosity of the porous β-TCP blocks was in the range of 69 to 77%. The porosity consisted of roughly 54% macropores (mean diameter close to 0.3-0.4 mm) and 25-33% micropores (mean diameter in the range of 1-10 micrometers)

The samples were calcined at 500° C. for 1 h prior to the impregnation tests to remove organic residues present on the block surface (without calcination, the samples were so hydrophobic that they were floating in aqueous solutions).

Impregnation tests were performed with a 0.25 g/mL. calcium chloride solution ($CaCl_2$).

Each of the 14×14 mm cylinders was placed standing in a snap cap flask. The solution (kept at 95° C.) was then slowly injected at the bottom of the snap-cap flask to allow impregnation through capillarity. 2 different volumes were injected: 10.5 and 14 mL.

Three cylinders were prepared for each solution volume. The cylinder top was always protruding out of the solution. The samples were then inserted into the drying cupboard tempered at 95° C. The ventilation of the drying cupboard was set at its maximum.

The weight of the flask+solution+samples was measured at regular interval to determine the point at which constant weight was reached. After 24 h, the samples were dry. The sample weight was determined to assess how much di-potassium hydrogen phosphate was present in the block pores.

Each sample was then placed into a small porous cage produced by joining together two BD Falcon filters (Mesh size: 70 micrometers). The cage was lowered into a 1 L deionized water. Stirring was performed with a large magnetic bar (6 cm in length) at 50 RPM. The samples were removed from the solution after 10 min, 1 h or 6 h (1 samples per time and per composition). The samples were then dried at 95° C. and weighed to determine the amount of $CaCl_2$ released during the incubation.

As control group, 6 β-TOP blocks that had not been impregnated in calcium chloride solution were also tested.

Results

The solution was sucked by the porous block within seconds. Since an excess of liquid was used, some solution was left besides the samples. Between 1.38 and 1.64 g calcium chloride could be loaded into the blocks. Despite a difference in the initial volume (10.5 or 14 mL), the loaded calcium chloride did not vary much, suggesting that a loading plateau is reached. Using the density of calcium chloride, it could be calculated that 42 to 47% of the pore volume was filled with calcium chloride.

The release rate was very fast, with roughly 50% released within 10 minutes and 80-85% after 1 h. At 6 h, the samples were free of calcium chloride. In other words, 1.38 to 1.64 grams of calcium chloride were dissolved within 6 h. Contrarily, the mean weight loss of pure β-TCP blocks (without calcium chloride) was slightly positive after 6 h (0.01±0.01 g) but not significantly larger than zero, which means that the dissolution rate $DR_D$ of calcium chloride was more than 100 times larger than the dissolution rate $DR_S$ of β-TCP.

Example 5

Aim

Load porous β-TCP blocks with $Na_2HPO_4.2H_2O$ and measure the $Na_2HPO_4.2H_2O$ release rate

Materials and Methods

The porosity of the porous β-TCP blocks was in the range of 69 to 77%. The porosity consisted of roughly 54% macro pores (mean diameter close to 0.3-0.4 mm) and 25-33% micropores (mean diameter in the range of 1-10 micrometers)

The samples were calcined at 500° C. for 1 h prior to the impregnation tests to remove organic residues present on the block surface (without calcination, the samples were so hydrophobic that they were floating in aqueous solutions).

Impregnation tests were performed with a 0.50 g/mL $Na_2HPO_4.2H_2O$ solution ($Na_2HPO_4.2H_2O$).

Each of the 14×14 mm cylinders was placed standing in a Petri dish (Inner dimensions: diameter: 8.7 cm; height: 1.1 cm). 24.3 mL of the solution (kept at 95° C.) was slowly injected at the bottom of the petri dish. The blocks were then press-fitted into a plastic membrane covering the Petri dish (FIG. 1). The bottom of the samples touched the bottom of the Petri dish, whereas the cylinder top protruded out of the membrane covering the Petri dish. The Petri dish+samples were then inserted into the drying cupboard tempered at 95° C. The ventilation of the drying cupboard was set at its maximum.

The weight of the flask+solution+samples was measured at regular interval to determine the point at which constant weight was reached. The sample weight was determined to assess how much $Na_2HPO_4.2H_2O$ was present in the block pores.

Results

The solution was sucked by the porous block within seconds. The samples could be loaded with the $Na_2HPO_4.2H_2O$ crystals, but large agglomerates were present on the block surface and quite some crystals remained at the bottom of the Petri dish, Large differences of loaded amount were observed, since values ranged from 0.7 to 1.2 g.

While various descriptions of the present invention are described above, it should be understood that the various features can be used singly or in any combination thereof. The scope of the present invention is accordingly defined as set forth in the appended claims.

What is claimed is:

1. A bone graft substitute in the form of an implantable three-dimensional scaffold comprising calcium phosphate and having pores, wherein:
   (i) the scaffold is impregnated with a calcium and/or phosphate containing substance, said calcium and/or phosphate containing substance having a solubility in an aqueous solution having a physiological ionic strength and a pH of 7.4 at 37° C. in a range between 2 mM and 1 M;
   (ii) a dissolution rate $DR_S$ of said scaffold is slower than a dissolution rate $DR_D$ of said calcium and/or phosphate containing substance used to impregnate the scaffold;
   (iii) a chemical composition and integrity of the scaffold remains essentially unaffected by said impregnation with said calcium and/or phosphate containing substance; and
   (iv) a degree of porosity of said scaffold is in a range of 40% to 95%.

2. The bone graft substitute according to claim 1, wherein said calcium and/or phosphate containing substance is ionic.

3. The bone graft substitute according to claim 1, wherein said calcium and/or phosphate containing substance is crystalline.

4. The bone graft substitute according to claim 3, wherein said calcium and/or phosphate containing substance has a degree of crystallinity higher than 80%.

5. The bone graft substitute according to claim 1, wherein said calcium and/or phosphate containing substance is not chemically bound to said scaffold.

6. The bone graft substitute according to claim 1, wherein said calcium and/or phosphate containing substance only adheres physically to said scaffold.

7. The bone graft substitute according to claim 1, wherein said dissolution rate $DR_D$ as measured in a phosphate-buffered solution (PBS) at pH 7.4 is at least 10 times larger than said dissolution rate $DR_S$.

8. The bone graft substitute according to claim 1, wherein said dissolution rate $DR_D$ as measured in an aqueous citric acid solution at pH 3.0 is at least 10 times larger than said dissolution rate $DR_S$.

9. The bone graft substitute according to claim 1, wherein said dissolution rate $DR_S=0$ and said dissolution rate $DR_D>0$ in serum or simulated body fluid having a pH 7.4 at 37° C. and 5% $CO_2$ in the atmosphere.

10. The bone graft substitute according to claim 1, wherein said calcium and/or phosphate containing substance is rigid.

11. The bone graft substitute according to claim 1, wherein said scaffold has micropores with a mean diameter $D_{micro}$ smaller than 10 microns.

12. The bone graft substitute according to claim 1, wherein said scaffold has macropores with a mean diameter $D_{macro}$ in the range of 0.03 to 1 mm.

13. The bone graft substitute according to claim 1, wherein said scaffold has a specific surface area superior to 1 $m^2$/g.

14. The bone graft substitute according to claim 1, wherein the tortuosity of the pores of said scaffold is larger than 3.

15. The bone graft substitute according to claim 1, wherein said pores are interconnected.

16. The bone graft substitute according to claim 12, wherein the size of interconnections between the pores is larger than 30 microns.

17. The bone graft substitute according to claim 1, wherein said calcium and/or phosphate containing substance comprises calcium chloride.

18. The bone graft substitute according to claim 1, wherein said calcium and/or phosphate containing substance comprises $K_2HPO_4$.

19. The bone graft substitute according to claim 1, wherein the ratio WD/WS between the weight WD of said calcium and/or phosphate containing substance and the weight WS of said scaffold is comprised in the range of 0.1 to 0.

20. The bone graft substitute according to claim 1, wherein said calcium phosphate of said scaffold is beta-tricalcium phosphate (β-TCP).

21. The bone graft substitute according to claim 1, wherein said scaffold has a volume larger than 10 $mm^3$.

22. The bone graft substitute according to claim 1, wherein said pores are filled with said calcium and/or phosphate containing substance to an extent of 1% to 50% by volume.

23. A method for manufacturing a bone graft substitute, the method comprising:

providing a three-dimensional scaffold comprising calcium phosphate having interconnected pores, and a calcium an/or phosphate containing substance having a solubility in an aqueous solution having a physiological ionic strength and a pH of 7.4 at 37° C. in a range between 2 mM and 1 M; and impregnating the three-dimensional scaffold comprising calcium phosphate having interconnected pores with the calcium and/or phosphate containing substance;

wherein a dissolution rate $DR_S$ of said scaffold is slower than a dissolution rate $DR_D$ of said calcium and/or phosphate containing substance used to impregnate the scaffold, wherein a degree of porosity of said scaffold is in a range of 40% to 95%, and wherein a chemical composition and integrity of said scaffold remains essentially unaffected by said impregnation with said calcium and/or phosphate containing substance.

24. The method according to claim 23, wherein the calcium and/or phosphate containing substance is calcium chloride and the impregnating is performed by applying an aqueous solution of calcium chloride to said scaffold.

25. The method according to claim 23, wherein the calcium and/or phosphate containing substance is $K_2HPO_4$ and the impregnating is performed by applying an aqueous solution of calcium chloride to said scaffold.

26. The method according to claim 23, wherein said aqueous solution applied to said scaffold is dried in an atmosphere having a relative humidity of 0%.

27. The method according to claim 23, wherein said aqueous solution applied to said scaffold is dried for more than 1 day.

28. The method according to claim 23, wherein said aqueous solution has a concentration of 12.5% to 50%.

29. The method according to claim 23, wherein said impregnating is performed in two successive steps.

30. The method according to claim 29, wherein one step of the two successive steps comprises impregnating the scaffold with a calcium-containing substance and another step of the two successive steps comprises impregnating the scaffold with a phosphate-containing substance.

* * * * *